US012687535B2

(12) United States Patent
Liu et al.

(10) Patent No.: US 12,687,535 B2
(45) Date of Patent: Jul. 21, 2026

(54) SYSTEM AND METHOD TO MEASURE CATION EXCHANGE CAPACITY

(71) Applicant: ARAMCO SERVICES COMPANY, Houston, TX (US)

(72) Inventors: Chao Liu, Brookshire, TX (US); Dung T. Phan, Brookshire, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 674 days.

(21) Appl. No.: 18/188,843

(22) Filed: Mar. 23, 2023

(65) Prior Publication Data

US 2024/0319161 A1    Sep. 26, 2024

(51) Int. Cl.
*G01N 33/24*         (2006.01)
(52) U.S. Cl.
CPC ..................................... *G01N 33/24* (2013.01)
(58) Field of Classification Search
CPC ....................................................... G01N 33/24
See application file for complete search history.

(56) References Cited

U.S. PATENT DOCUMENTS

| | | | | |
|---|---|---|---|---|
| 5,005,403 | A  * | 4/1991 | Steudle .................. | G01N 13/04 |
| | | | | 73/61.78 |
| 2015/0315045 | A1* | 11/2015 | Sanborn .................... | A62D 3/38 |
| | | | | 210/759 |
| 2020/0398221 | A1* | 12/2020 | Arias-Paic ........... | B01D 15/203 |
| 2022/0145751 | A1* | 5/2022 | Liu ........................... | G01V 5/12 |

FOREIGN PATENT DOCUMENTS

| | | | | |
|---|---|---|---|---|
| JP | 2000088744 A | * | 3/2000 | |
| KR | 20210023691 A | * | 3/2021 | ............. B01D 65/08 |

OTHER PUBLICATIONS

M. Bergoglio "Intercomparison of gas flow-rate measurements at IMGC, Italy, and UASG, Germany, in the range from 10-8 to 10-3 Pa m3/s", pp. 561-567 (Year: 2006).*

Liu et al., "Theory and analytical solutions to coupled processes of transport and deformation in dual-porosity dual-permeability poro-chemo-electro-elastic media," Journal of Applied Mechanics, Jul. 2018, 14 pages.

Luo et al., "Determination of shale osmotic pressure using spontaneous potential log," Environmental Earth Science, Dec. 22, 2016, 8 pages.

Nguyen et al., "Incorporating electrokinetic effects in the porochemoelastic inclined wellbore formulation and solution," Anais da Academia Brasileira de Ciencias. 82(1), 195-222, Sep. 10, 2008, 28 pages.

* cited by examiner

*Primary Examiner* — Michael J Dalbo
*Assistant Examiner* — Kaleria Knox
(74) *Attorney, Agent, or Firm* — Osha Bergman Watanabe & Burton LLP

(57)         ABSTRACT

A system for determining cation exchange capacity includes: a container containing a solution having a solute and a solvent; a sample; a pressure sensor configured to measure an osmotic pressure of the sample generated by a flow of the solution through the sample; and a control unit configured to determine the cation exchange capacity of the sample based on the osmotic pressure measured by the pressure sensor.

16 Claims, 3 Drawing Sheets

SYSTEM AND METHOD TO MEASURE CATION EXCHANGE CAPACITY

BACKGROUND

Clay or organic matters in a reservoir or rock sample have negative charges ($X^{n-}$) on their surfaces which adsorb and hold positively charged ions (cations, e.g., $Ca^{2+}$, $Mg^{2+}$, $Na^+$, and $K^+$) by electrostatic force. Cation exchange capacity (CEC) is one of the parameters that is useful for identifying physical and chemical properties of these surfaces. Specifically, cation exchange capacity is a measure of quantity of cations that a reservoir or rock sample can accommodate on its negatively charged surfaces, expressed as million equivalent per 100 g, or more commonly as milliequivalent (meq) per 100 g.

The cation exchange capacity of a sample may conventionally be determined by a wet chemistry method. However, the cation exchange capacity determined by a wet chemistry method is not reservoir representative for the following reasons: (1) the sample is cleaned to remove any oil in the sample, which is not representative of the in-situ reservoir conditions; (2) the sample is ground to fine particles, however excessive grinding will increase the cation exchange capacity by exposing more cation exchange sites than the case at the in-situ reservoir conditions, resulting in the overestimation cation exchange capacity, while insufficient grinding will lead to some reservoir representative cation exchange sites not being exposed, resulting in underestimation of the cation exchange capacity; and (3) the accuracy of the measurements highly depends on the accuracy of the measurements of the chemicals. For example, the reliability may be affected by purity of deionized water, pH of ammonium acetate solution, and particle size of the sample. Moreover, the inductively-coupled plasma mass spectrometry (ICP-MS) measurements used in wet chemistry method are sensitive to any contamination of ions.

As such, there exists a need to develop a system and a method for accurately and efficiently measuring the cation exchange capacity.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In some aspects, embodiments described herein relate to a system for determining cation exchange capacity, including: a container containing a solution having a solute and a solvent; a sample; a pressure sensor configured to measure an osmotic pressure of the sample generated by a flow of the solution through the sample; and a control unit configured to determine the cation exchange capacity of the sample based on the osmotic pressure measured by the pressure sensor. In some embodiments, the sample includes at least one of soil and rock, and at least one of clay and an organic matter. In some embodiments, the solute includes one or more of NaCl, $MgCl_2$, and $CaCl_2$.

In some aspects, embodiments described herein relate to a system that further includes a tubing having two ends that connects the sample and the pressure sensor, wherein a first end of the tubing is arranged inside a cavity of the sample and a second end of the tubing is connected to the pressure sensor.

In some aspects, embodiments described herein relate to a system, wherein the container has an inlet configured to introduce the solution to the container and an outlet configured to guide the solution out of the container. The outlet may be exposed to an atmosphere. In some embodiments, a flow rate at the inlet and a flow rate at the outlet range from $10^{-4}$ m$^3$/s to $10^{-3}$ m$^3$/s. In some embodiments, a pressure change caused by the flow of the solution around the sample is negligible compared to atmosphere pressure.

In some aspects, embodiments described herein relate to a system, wherein the control unit is configured to determine the cation exchange capacity of the sample based on equation:

$$CEC = \frac{\phi}{10(1-\phi)\rho_s V_0^f} \sqrt{\left(\frac{V_0^f}{RT} p_{osmotic} + 2m_{sol}^s\right)^2 - 4(m_{sol}^s)^2}$$

where $$m_{sol}^s$$

is a concentration of the solute in the solution, $\rho_s$ is a grain density of the sample, $\phi$ is a porosity of the sample, $$V_0^f$$

is a partial molar volume of the solvent, R is universal gas constant which equals 8.314 J/K/mol, T is a temperature of the solution in Kelvin.

In some aspects, embodiments described herein relate to a method for determining cation exchange capacity, including: disposing a sample in a container; immersing the sample in a solution that includes a solute and a solvent; flowing the solution through the sample; measuring, using a pressure sensor, an osmotic pressure in the sample; and determining the cation exchange capacity of the sample based on the osmotic pressure measured by the pressure sensor. In some embodiments, the sample and the pressure sensor are connected by a tubing having two ends, wherein a first end of the tubing is arranged inside a cavity of the sample. The solution may be introduced to the container through an inlet of the container and the solution may be guided out of the container through an outlet of the container.

In some aspects, embodiments described herein relate to methods that further include controlling a flow rate at the inlet and a flow rate at the outlet, such that a pressure change caused by the flowing of the solution around the sample is negligible compared to atmosphere pressure.

In some aspects, embodiments described herein relate to a method that includes determining the cation exchange capacity of the sample is based on equation:

$$CEC = \frac{\phi}{10(1-\phi)\rho_s V_0^f} \sqrt{\left(\frac{V_0^f}{RT} p_{osmotic} + 2m_{sol}^s\right)^2 - 4(m_{sol}^s)^2}$$

where $$m_{sol}^s$$

is a concentration of the solute in the solution, $\rho_s$ is a grain density of the sample, $\phi$ is a porosity of the sample, $$V_0^f$$

is a partial molar volume of the solvent, R is universal gas constant which equals 8.314 J/K/mol, T is a temperature of the solution in Kelvin.

Other aspects and advantages of the claimed subject matter will be apparent from the following description and the appended claims.

DETAILED DESCRIPTION

Figure 1:
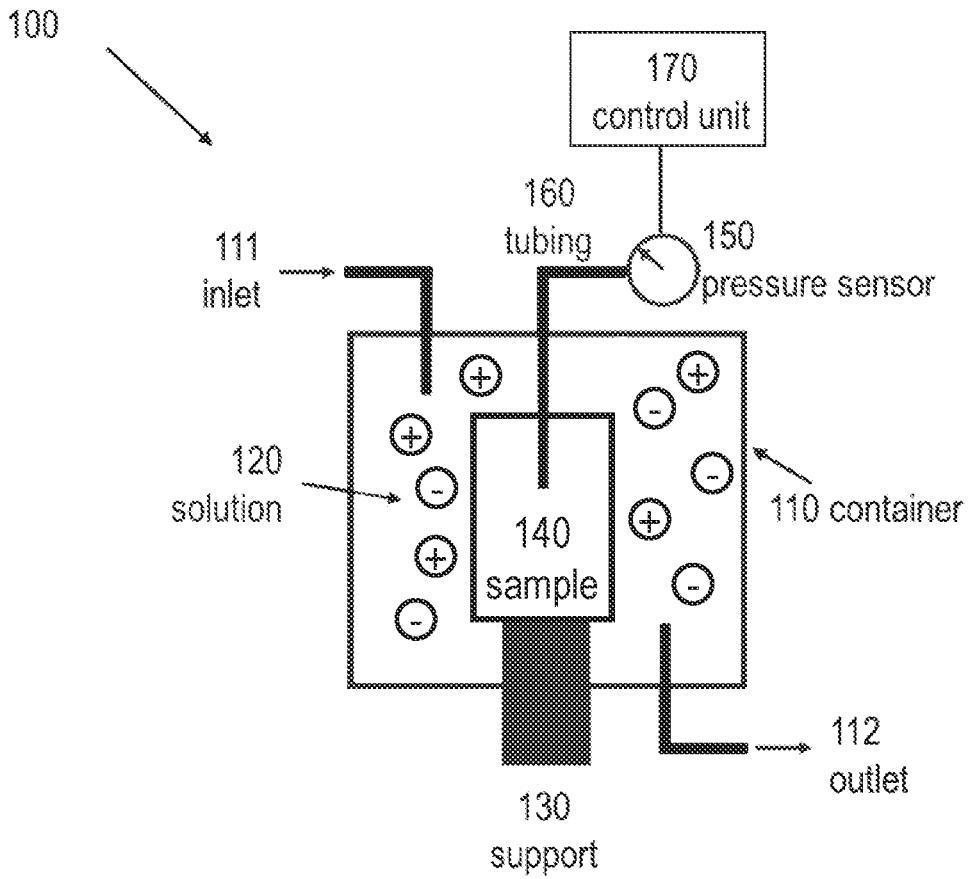
FIG. 1 shows an example of a system in accordance with one or more embodiments of the present disclosure.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

The cation exchange capacity is an essential property related to the osmotic pressure during wellbore drilling and could significantly impact wellbore stability. Before drilling, the formation is saturated with a pore fluid having an initial pore pressure $p_0$, anions with mole fraction $$m_0^a,$$

and cations with mole fraction $$m_0^c.$$

When cations are attracted onto the negatively charged surfaces of clay and organic matter in the formation, there is $$m_0^c > m_0^a.$$

After wellbore drilling, the borehole is filled with a drilling fluid having pressure $p_{mud}$ and solute mole fraction $$m_{mud}^s.$$

At an interface between a drilling mud and the formation, electrochemical potentials of all fluid species are continuous. As drilling continues and fluids/ions diffusion proceeds, the ions mole fractions in the formation pore fluid will be disturbed.

Accompanying the ions and solvent exchange between the mud and the pore fluid, an osmotic pressure may be generated that equals to:

$$p_{osmotic} = \frac{RT}{V_0^f}\left(\sqrt{(m^{fc})^2 + 4(m_{mud}^s)^2} - 2m_{mud}^s\right) \quad (1)$$

where R is universal gas constant, T is temperature, $$V_0^f$$

is partial molar volume of the solvent (such as water), $m^{fc}$ is mole fraction of fixed charges on the surfaces of clay and organic matter that equals to:

$$m^{fc} = \frac{10CEC(1 - \phi)\rho_s V_0^f}{\phi} \quad (2)$$

where $\phi$ is porosity and $\rho_s$ is density of the solid grains of the formation.

As shown by the above equations, cation exchange capacity (CEC) is a crucial parameter related to the osmotic pressure $p_{osmotic}$, therefore, impacting wellbore stability. Therefore, knowing the value of the cation exchange capacity is important for drilling processes through formations in oilfield applications.

Embodiments disclosed herein relate generally to systems and methods to determine a cation exchange capacity of a sample. Instead of measuring chemical contents to determine cation exchange capacity, as the conventional wet chemistry methods do, one or more embodiments of the present disclosure provide systems and methods to measure an osmotic pressure of a sample exposed to a solution with predetermined solute concentrations and predetermined pressure. Further, a calculation method is applied to calculate the cation exchange capacity based on the measured osmotic pore pressure.

FIG. 1 shows an example of a system in accordance with one or more embodiments of the present disclosure. The system 100 of the present disclosure may include a container for holding a solution 120. The container may have any shape or size of interest. In the non-limiting example of FIG. 1, the system 100 comprises a container 110 having a rectangular shape. The container includes at least a bottom surface and a plurality of side surfaces. In some embodiments, the container may also include a top surface or a lid, such that the container may form a closed system. The container may be made of any material as needed, as long as it is inert to the solution. The container 110 has an inlet 111 configured for introducing the solution to the container. The inlet may be arranged near or at a top portion of the container. The container 110 also has an outlet 112 that connects an interior of the container to an exterior of the container and guides the solution out of the container. The outlet may be arranged near or at a bottom portion of the container. In one or more embodiments, the outlet may connect the interior of the container to atmosphere. One or more connection members, such as tubings, valves, pipes, may be used in the inlet or outlet.

According to one or more embodiments, the solution 120 comprises one or more of solutes dissolved in one or more solvents. The solutes may contain one or more of NaCl, $MgCl_2$, and $CaCl_2$. A mole fraction of the solute in the solution may range from 0 to 0.3. The solvent may be water. In one or more embodiments, a concentration of each solute in the solution may be kept constant during a time of measurement. By keeping the concentration constant, an environment that the sample is exposed to is unchanged. In one or more embodiments, a flow rate of the solution in the container may be kept constant during a time of measurement. In other words, a flow rate at the inlet of the container and/or a flow rate at the outlet of the container may be kept constant during the time of measurement. In one or more embodiments, the flow rate at the inlet equals to the flow rate at the outlet and both flow rates are controlled simultaneously. In one or more embodiments, the flow rate at the inlet and the outlet are kept at a small value, such that the pressure change in the container caused by the flow of the solution is small, or even negligible, compared to the atmosphere pressure. That is, when the flow rates are small, a pressure inside the container is almost equal to the atmosphere pressure (i.e., 1 atm). In one or more embodiments, the flow rate may range from $10^{-4}$ $m^3$/s to $10^{-3}$ $m^3$/s.

According to one or more embodiments of the present disclosure, the system includes a support 130 for holding a sample 140. At least a portion of the support is arranged inside the container 110 and is entirely immersed in the solution 120. The portion of the support that is inside the container is inert to chemical solutions. In some embodiments, the support is fixed to the container through any manner commonly known to one having ordinary skill in the art.

According to one or more embodiments, the sample may be disposed on the support in the container and is entirely immersed in the solution. The sample may comprise one or more of soil, rock, human bone, and cartilage. For example, the sample may be a clay rich sedimentary rock, such as shale rock. In one or more embodiments, the sample may include clay in an amount of 40-60 weight percentage (wt %). In one or more embodiments, the sample may include organic matters, such as kerogen, rotted manure, and peat moss. The organic matters may be attached to a surface of the sample during oil production processes.

According to one or more embodiments, the system may include a tubing 160 having two ends. A first end of the tubing may be in direct contact with the sample 140. In one or more embodiments, the sample may have a cavity (such as a hole) drilled at one surface toward a center of the sample, where the first end of the tubing may be disposed inside the cavity, for example, near the center of the sample. A second end of the tubing 160 may connect to a pressure sensor 150. When the sample 140 is immersed in the solution 120, diffusion of ions and fluids in the solution 120 may take place, and an osmotic pressure may start to generate and accumulate in the sample 140, which can be recorded by the pressure sensor 150. In one or more embodiments, the pressure sensor may be a pressure gauge.

According to one or more embodiments, the system may include a control unit 170 for determining the cation exchange capacity based on the osmotic pressure recorded by the pressure sensor 150. For example, the control unit may include a computing device, providing computational functionalities associated with algorithms, methods, functions, processes, flows, and procedures as described in one or more embodiments of the present disclosure.

According to one or more embodiments, the computing device is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computing device may include a computer that includes an input device, such as a keypad, keyboard, touch screen, or other device that can accept user information, and an output device that conveys information associated with the operation of the computing device, including digital data, visual, or audio information (or a combination of information), or a GUI.

At a high level, the computing device is an electronic computing device operable to receive, transmit, process, store, or manage data and information associated with the described subject matter. According to some implementations, the computing device may also include or be communicably coupled with an application server, e-mail server, web server, caching server, streaming data server, business intelligence (BI) server, or other server (or a combination of servers). In one or more embodiments, the computing device may include at least one processor. Generally, the processor executes instructions and manipulates data to perform the operations of the computing device and any algorithms, methods, functions, processes, flows, and procedures as described in the instant disclosure. In one or more embodiments, the computing device may include a memory that holds data for the computing device. For example, the memory can be a database storing data consistent with this disclosure. In one or more embodiments, the computing device may include an application, which is an algorithmic software engine providing functionality according to particular needs, desires, or particular implementations of the computing device, particularly with respect to functionality described in the present disclosure.

Figure 2:
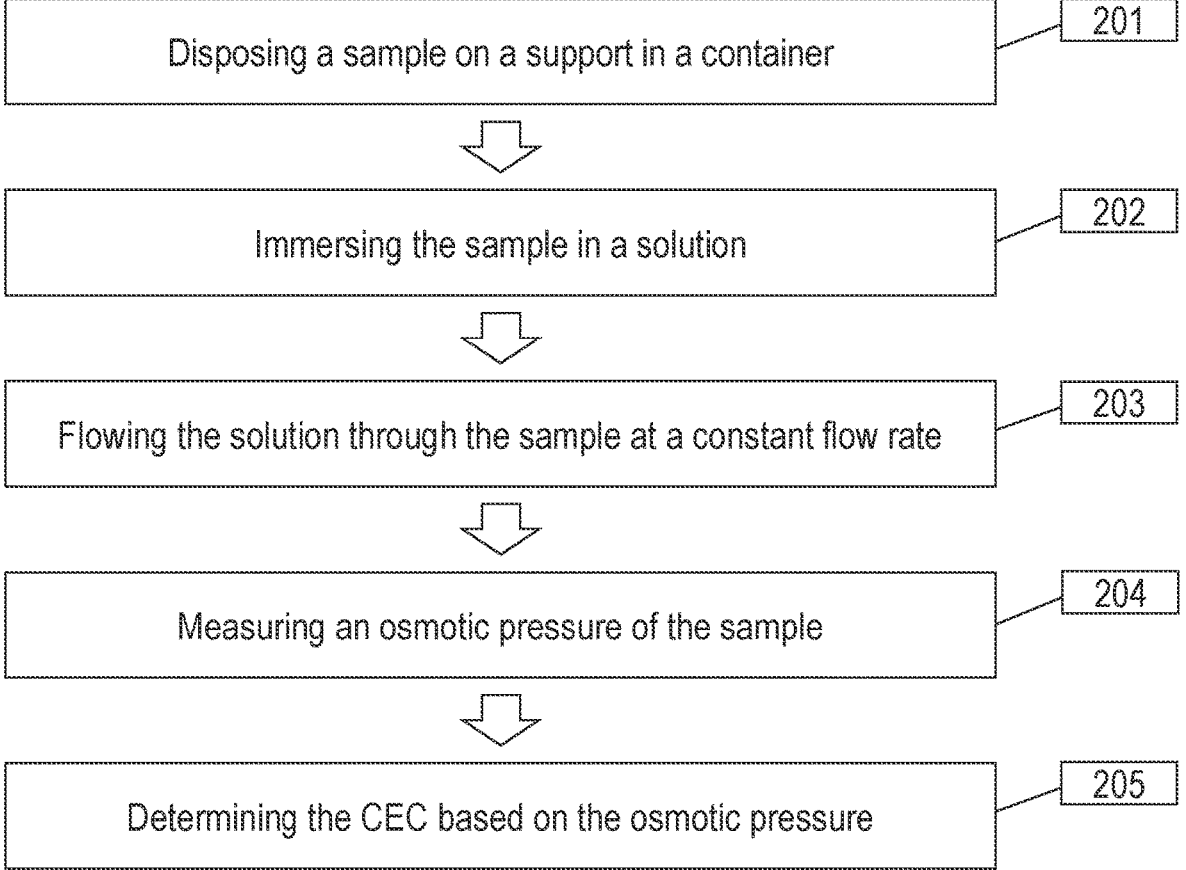
FIG. 2 shows a flowchart of a method in accordance with one or more embodiments.

Embodiments of the present disclosure may also relate to methods for determining cation exchange capacity, which may be associated with one or more functionalities provided by the system described in the present disclosure. For example, FIG. 2 shows a flowchart of a method in accordance with one or more embodiments. One or more blocks in FIG. 2 may be performed by one or more components as described in FIG. 1.

In one or more embodiments, the method may include step 201, disposing a sample in a container. The sample may be disposed on a support. The container and the support may have configurations as described in one or more embodiments of the present disclosure.

In one or more embodiments, the method may include step 202, immersing the sample in a solution. For example, the sample may be immersed in a solution by disposing the sample in a container that is already filled with the solution. The sample may be a soil sample or a rock sample and may include clay or organic matters. The solution may include solutes, such as NaCl, $MgCl_2$, and $CaCl_2$, at a mole fraction ranging from 0 to 0.3.

In one or more embodiments, the method may include step 203, flowing the solution having a constant solute concentration through the sample at a constant flow rate. The solution may be introduced through an inlet of the container, where the inlet may have configurations as described in one or more embodiments of the present disclosure. During the flowing, ions and fluids in the solution may diffuse into the sample, generating and accumulating a measurable osmotic pressure. The solution exits the container through an outlet. By controlling a flow rate at the inlet and a flow rate at the outlet, a flow rate of the solution flowing through the container is controlled to be constant and is kept at a small value, such that the pressure change inside the solution caused by the flowing of the solution is small, or even negligible, compared to the atmosphere pressure. In other words, the pressure that the sample is exposed to is constant and almost equals the atmosphere pressure.

In one or more embodiments, the method may include step 204, measuring an osmotic pressure of the sample. A pressure sensor may be used to measure the osmotic pressure of the sample through a tubing. The tubing has a first end that is in direct contact with the sample and a second end connected to the pressure sensor. In one or more embodiments, the osmotic pressure inside the sample is measured. Specifically, the sample may have a cavity (such as a hole), and the tubing may be disposed inside the cavity, such that the osmotic pressure near a center of the sample is recorded. In some embodiments, the inner diameter of a hole in the sample may be close to but slightly larger than the outer diameter of the tubing, such that the first end of the tubing snuggly fits within the hole.

In one or more embodiments, the method may include step 205, determining the cation exchange capacity of the sample based on the osmotic pressure measured by the pressure sensor. The cation exchange capacity (CEC) may be determined using the following equation:

$$CEC = \frac{\phi}{10(1-\phi)\rho_s V_0^f} \sqrt{\left(\frac{V_0^f}{RT}p_{osmotic} + 2m_{sol}^s\right)^2 - 4(m_{sol}^s)^2} \quad (3)$$

where $$m_{sol}^s$$

is concentration of a solute in the solution, $\rho_s$ is grain density of the sample, $\phi$ is porosity of the sample, $$V_0^f$$

is partial molar volume of solvent which may be $18 \times 10^{-3}$ liter/mol for water, $p_{osmotic}$ is the osmotic pressure measured by the pressure sensor, R is universal gas constant which is 8.314 J/K/mol, T is a temperature of the solution in Kelvin. The grain density $\rho_s$ of the sample, which refers to a density of the sample without considering porosity, may be obtained with a dried sample. The porosity $\phi$ of the sample can be measured using nuclear magnetic resonance (NMR) method or determined from neutron porosity log from the oilfield. The temperature T may be room temperature (or ambient temperature) and may be in a range of 15-25° C. if no additional temperature control device is applied.

While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

According to one or more embodiments, the systems and methods described in the present disclosure relates to determining the cation exchange capacity based on osmosis pressure. Because the sample contains clay which have negatively charged surfaces, cations are attracted to these surfaces to balance the negative fixed charges. Consequently, ions concentration near the negatively charged surfaces becomes higher than that near surfaces that are not negatively charged. As a result, an osmotic pressure between the two is generated and may be measured for determining the cation exchange capacity (CEC).

Example 1

A non-limiting example in accordance with one or more embodiments of the present disclosure is described for illustrative purposes.

Figure 3:
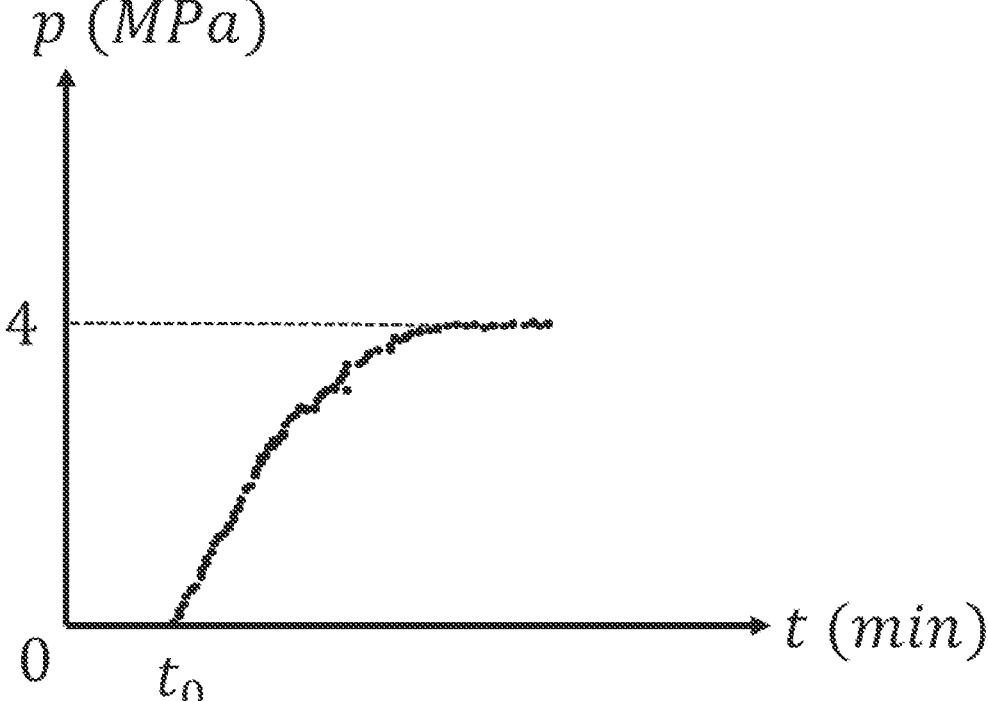
FIG. 3 shows an example of measured data using systems and methods in accordance with one or more embodiments.

A sample containing a shale rock was disposed in the system, as described in FIG. 1 and one or more embodiments the present disclosure, for osmotic pressure measurement. A porosity of the shale rock was measured to be 0.12. A grain density of the shale rock was 2.5 grams per cubic centimeter (g/cc or g/cm$^3$). A temperature was measured to be 77° F., that is, 298.15 K. A mole fraction of the solute in the solution was 0.08. An illustration of the osmotic pressure recorded from a pressure gauge is presented in FIG. 3. As fluid and ions diffusion take places, the pore pressure inside the sample starts to increase at time to. As time proceeds, the osmotic pressure increases and reaches an equilibrium (dash line). The equilibrium value of the osmotic pressure was equal to 4 MPa. Using the above measured parameters, the cation exchange capacity (CEC) of the shale rock was determined according to equation (3) as 8.9 meq/100 g.

$$CEC = \frac{0.12}{10 \times (1-0.12) \times 2.5 \times 18 \times 10^{-3}} \times \quad (4)$$
$$\sqrt{\left(\frac{18 \times 10^{-3}}{8.314 \times 298.15} \times 4 \times 10^6 + 2 \times 0.08\right)^2 - 4 \times 0.08^2} = 8.9 \text{ meq/100 g}$$

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A system for determining cation exchange capacity, comprising:
   a container containing a solution, the solution includes a solute and a solvent;
   a sample;
   a pressure sensor configured to measure an osmotic pressure of the sample generated by a flow of the solution through the sample; and
   a control unit configured to determine the cation exchange capacity of the sample based on the osmotic pressure measured by the pressure sensor, wherein the control unit is configured to determine the cation exchange capacity of the sample based on equation:

$$CEC = \frac{\phi}{10(1-\phi)\rho_s V_0^f} \sqrt{\left(\frac{V_0^f}{RT}p_{osmotic} + 2m_{sol}^s\right)^2 - 4(m_{sol}^s)^2}$$

where $$m_{sol}^s$$

is a concentration of the solute in the solution, $\rho_s$ is a grain density of the sample, $\phi$ is a porosity of the sample, $$V_0^f$$

is a partial molar volume of the solvent, R is universal gas constant which equals 8.314 J/K/mol, T is a temperature of the solution in Kelvin.

2. The system of claim 1, wherein the sample comprises at least one of soil and rock, and at least one of clay and an organic matter.

3. The system of claim 1, wherein the solute comprises one or more of NaCl, $MgCl_2$, and $CaCl_2$).

4. The system of claim 1, further comprises a support fixed to the container and configured to hold the sample.

5. The system of claim 1, further comprises a tubing having two ends that connects the sample and the pressure sensor, wherein a first end of the tubing is arranged inside a cavity of the sample and a second end of the tubing is connected to the pressure sensor.

6. The system of claim 1, wherein the container has an inlet configured to introduce the solution to the container and an outlet configured to guide the solution out of the container.

7. The system of claim 6, wherein the outlet is exposed to an atmosphere.

8. The system of claim 6, wherein a flow rate at the inlet and a flow rate at the outlet range from $10^{-4}$ m³/s to $10^{-3}$ m³/s.

9. The system of claim 6, wherein a pressure change caused by the flow of the solution around the sample is negligible compared to atmosphere pressure.

10. A method for determining cation exchange capacity, comprising:
    disposing a sample in a container;

immersing the sample in a solution that includes a solute and a solvent;

flowing the solution through the sample;

measuring, using a pressure sensor, an osmotic pressure in the sample; and determining the cation exchange capacity of the sample based on the osmotic pressure measured by the pressure sensor, wherein the determining the cation exchange capacity of the sample is based on equation:

$$CEC = \frac{\phi}{10(1-\phi)\rho_s V_0^f} \sqrt{\left(\frac{V_0^f}{RT}p_{osmotic} + 2m_{sol}^s\right)^2 - 4(m_{sol}^s)^2}$$

where $$m_{sol}^s$$

is a concentration of the solute in the solution, $\rho_s$ is a grain density of the sample, $\phi$ is a porosity of the sample, $$V_0^f$$

is a partial molar volume of the solvent, R is universal gas constant which equals 8.314 J/K/mol, T is a temperature of the solution in Kelvin.

11. The method of claim 10, wherein the sample comprises at least one of soil and rock, and at least one of clay and an organic matter.

12. The method of claim 10, wherein the solute comprises one or more of NaCl, $MgCl_2$, and $CaCl_2$).

13. The method of claim 10, further comprises connecting the sample and the pressure sensor by a tubing having two ends, wherein a first end of the tubing is arranged inside a cavity of the sample.

14. The method of claim 10, further comprising introducing the solution to the container through an inlet of the container and guiding the solution out of the container through an outlet of the container.

15. The method of claim 14, wherein the outlet is exposed to an atmosphere.

16. The method of claim 14, further comprising controlling a flow rate at the inlet and a flow rate at the outlet, such that a pressure change caused by the flowing of the solution around the sample is negligible compared to atmosphere pressure.

* * * * *